United States Patent [19]

Samain et al.

[11] Patent Number: 5,628,991
[45] Date of Patent: May 13, 1997

[54] COSMETIC COMPOSITION CONTAINING A DIAMINOALKANE AS AN ODORLESS ALKALIFYING AGENT

[75] Inventors: Henri Samain, Bievres; Claude Dubief, Le Chesnay; Jean Cotteret, Verneuil S/Seine, all of France

[73] Assignee: L'Oreal, Paris, France

[21] Appl. No.: 437,970

[22] Filed: May 10, 1995

Related U.S. Application Data

[63] Continuation of Ser. No. 286,169, Aug. 5, 1994, abandoned, which is a continuation of Ser. No. 878,493, May 5, 1992, abandoned.

[30] Foreign Application Priority Data

May 6, 1991 [FR] France ................. 91 05503

[51] Int. Cl.[6] ................................ A61K 7/06
[52] U.S. Cl. .............. 424/70.1; 424/70.51; 424/70.5; 424/70.2; 424/70.11; 424/DIG. 1; 424/DIG. 3
[58] Field of Search ....................... 424/73, DIG. 1, 424/DIG. 2, DIG. 3, 78.03, 70.11, 70.51, 70.5, 70.2, 70.1, 70.02, 70.03

[56] References Cited

U.S. PATENT DOCUMENTS 5,085,860  2/1992  Junino et al. ............... 424/73

FOREIGN PATENT DOCUMENTS 1146332  11/1957  France .
2188948  10/1987  United Kingdom .

OTHER PUBLICATIONS

Patent Abstracts of Japan, (C–572), Feb. 1989.

Rauino et al, "Independent induction and inhibition of ornithine decarboxylase and aryl hydrocarbon hydroxylase activities in rat epidermis" Chem. Abstracts, vol. 97, No. 25 Dec. 1982, p. 254, Abstract. No. 209789m, & Invest. Dermatol. 1982, 79(4) 246–9.

*Primary Examiner*—Raj Bawa
*Attorney, Agent, or Firm*—Cushman Darby & Cushman Intellectual Property Group of Pillsbury Madison & Sutro LLP

[57] ABSTRACT

A cosmetic composition for treatment of human keratinous organs is na aqueous medium having a pH ranging from 5 to 12.5 and contains (a) as an active agent a reducing agent, a dyeing agent or an oxidizing agent and (b) a diaminoalkane which combats or reduces residual unpleasant odor of human keratinous organs treated with the active agent.

7 Claims, No Drawings

COSMETIC COMPOSITION CONTAINING A DIAMINOALKANE AS AN ODORLESS ALKALIFYING AGENT

This is a continuation of application Ser. No. 08/286,169, filed Aug. 5, 1994, now abandoned, which is a continuation of application Ser. No. 07/878,493, filed May 5, 1992, now abandoned.

The invention relates to a cosmetic composition including at least one practically odorless alkalifying agent.

It is known that cosmetic compositions intended for the treatment of human keratinous materials such as hair, body hair or the skin generally contain at least one alkalifying agent intended to bring the pH of the composition to a value which is generally between 5 and 12.5. In the case of compositions which have a basic pH the part played by the alkalifying agent differs according to the type of composition concerned: in the case of some compositions using aqueous hydrogen peroxide as oxidizing agent the aqueous hydrogen peroxide needs to be brought to a basic pH to permit its decomposition; in the case of compositions intended for treating hair in general, the adoption of a basic pH makes it possible to dilate the cuticle sheath of the hair and facilitate the entry of the treatment agents inside the said sheath. These two effects are encountered individually or simultaneously in most of the applications of cosmetic compositions, be they hair removers, coloring or bleaching compositions for hair, pigmenting or depigmenting compositions for the skin or compositions for permanent deformation of hair, for permanent waving or for straightening.

The alkalifying agents generally employed in cosmetic compositions in the state of the art are either aqueous ammonia or monoethanolamine. In both cases, these agents have an unpleasant odor which is inconvenient for the user. Aqueous ammonia gives off a strong, pungent and suffocating odor; it is particularly inconvenient in hairdressing salons for the users of permanent waving, coloring or bleaching products. Furthermore, monoethanolamine does not always make it possible to reach relatively high basic pHs. It is a fact that, in some of the abovementioned cosmetic compositions, for example hair-removing compositions or permanent waving compositions, reducing agents are employed which, in themselves, have a fairly unpleasant odor; nevertheless, the use of malodorous alkalifying agents merely reinforces the abovementioned olfactory disadvantage in the case of the said compositions.

According to the invention it has been found that it is possible to employ, as alkalifiers for cosmetic compositions, certain diaminoalkanes which not only have the advantage of not being malodorous in themselves but which, in addition, have the advantage of giving advantageous and unexpected additional results; the said results are diversified according to the intended use of the cosmetic compositions in question:

a) when a cosmetic composition intended for the permanent waving of hair is involved, it has been found that, with the alkalifiers proposed according to the invention, the curliness is at least as tight as that obtained with the reducing compositions of the prior art containing aqueous ammonia, and is very markedly tighter than that employing monoethanolamine; in addition, the mechanical properties of hair subjected to the permanent waving are retained better with the alkalifiers proposed according to the invention; moreover, it has been found that when the reducing composition of the permanent wave contains cysteamine, it is possible, by treating the hair with a solution containing at least one diaminoalkane, before or after the application of the permanent waving or between the two stages of reduction and fixing of the permanent waving, to combat the residual unpleasant odor impregnating the hair;

b) when compositions for coloring hair are involved it is found that, with the alkalifiers proposed according to the invention, colorings are obtained which have the advantage of causing less damage to the hair fiber, it being possible for the said colorings to be as powerful in certain cases as those of the prior art employing aqueous ammonia;

c) when compositions for bleaching hair or for lightening the hair color are involved, it has been found that, with the alkalifiers proposed according to the invention, they have a lightening power which is at least equal to that of analogous compositions alkalified with aqueous ammonia;

d) when compositions for removing hair are involved, it has been found that the use of the alkalifiers proposed according to the invention makes it possible to obtain compositions which are less irritant to the skin than those containing monoethanolamine.

The objective of the present invention is therefore the use, as an odorless alkalifying agent in cosmetic compositions, of a particular category of diaminoalkanes corresponding to the formula (I) defined below.

The subject of the present invention is a cosmetic composition intended to be applied to a human keratinous organ such as the skin, hair and body hair, comprising, in an aqueous medium with a basic pH, on the one hand, an active agent suitable for the said treatment and, on the other hand, an alkalifying agent, characterized in that the alkalifying agent consists of at least one compound of formula (I):

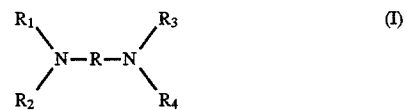

in which formula:

R is a propylene residue optionally substituted by a hydroxyl group or a $C_1$–$C_4$ alkyl radical;

$R_1$, $R_2$, $R_3$ and $R_4$, simultaneously or independently of each other, denote hydrogen or a $C_1$–$C_4$ alkyl or hydroxyalkyl ($C_1$–$C_4$) radical.

In a preferred embodiment the alkalifying agent comprises at least one compound chosen from the group consisting of 1,3-diaminopropane, N,N'-diethyl-1,3-diaminopropane, N,N-diethyl-1,3-diaminopropane, N,N-dimethyl-1,3-diaminopropane, 2-hydroxy-1-(N,N-diethyl)amino-3-aminopropane, 2-hydroxy-N,N'-di-tert-butyl-1,3-diaminopropane, 2-hydroxy-N,N'-tetramethyl-1,3-diaminopropane and 2-hydroxy-1,3-diaminopropane.

In a first alternative form of embodiment of the invention the cosmetic composition is intended to be employed for the permanent deformation of hair or hair removal; in this case it comprises a reducing agent as active agent; the reducing agent preferably comprises at least one compound chosen from the group consisting of thioglycolic acid, thiolactic acid, cysteamine, cysteine, 4-hydroxy-N-(2-mercaptoethyl) butyramide and the N-mono or N,N-disubstituted 4-mercaptobutyramides described in Application EP 638, 763. When a composition for permanent deformation of the hair is involved the pH is generally between 5 and 10; when a hair-removing composition is involved the pH is generally between 9 and 12.5.

In the case of permanent waving compositions employing cysteamine or one of its salts as reducing agent, the application of an aqueous solution of diaminoalkanes of formula (I) in sufficient quantity for the pH to be higher than 7 and preferably higher than 8, before or after the permanent waving, or between the two reduction/fixing stages of the permanent waving, makes it possible to combat the residual unpleasant odor impregnating the hair, which is particularly noticeable when the treated hair is in a wet state or in a moist environment. It is preferred to perform a pretreatment, that is to say an application before the permanent waving.

In a second alternative form, the composition according to the invention is intended to be employed for dyeing the hair; in this case it comprises an active agent consisting of at least one dyeing compound chosen from the group consisting of oxidation dye precursors, couplers, rapid oxidation dyes and melanic pigment precursors; the dyeing compound(s) is(are) preferably chosen from the group consisting of ortho- or para-phenylenediamines, ortho- or para-aminophenols, aromatic meta-diamines, meta-aminophenols, meta-diphenols, 5,6-dihydroxyindole and its derivatives; the pH of such a composition is generally adjusted between 5 and 11.

According to a third alternative form the composition according to the invention is intended for bleaching hair or for lightening the color of hair; in this case the composition comprises a powerful oxidizing agent as active agent; the pH of such a composition is generally between 7 and 12.

Depending on the type of composition concerned, the pH of the compositions according to the invention is obtained by adding more or less considerable quantities of diaminoalkanes of formula (I). For example, in compositions intended for permanent waving of hair, from 3.7 to 12% by weight of the alkalifying agent is generally employed to obtain the desired pH by adding 1,3-diaminopropane, this percentage being given in relation to the total weight of the composition. When the composition according to the invention is intended for coloring or bleaching hair, the same alkalifying agent as mentioned above is employed in proportions which are preferably between 4 and 10% by weight relative to the total weight of the composition. The figures given above are not limiting in any way and depend essentially, on the one hand, on the use of the cosmetic composition in question and, on the other hand, on the nature of the active agents or the adjuvants present in the composition and, lastly, on the alkalifying compound(s) chosen from all the compounds of formula (I).

To make the subject matter of the invention better understood, a number of methods of implementing the invention will be described below by way of examples, purely as an illustration and without any limitation being implied.

EXAMPLES 1 TO 6

Six reducing compositions intended for permanent waving of hair were formulated by employing, in the case of each one, a compound of formula (I) as alkalifying agent. The formulations thus produced are given in grams in Table I below:

TABLE I

| Example No. | 1 | 2 | 3 | 4 | 5 | 6 |
|---|---|---|---|---|---|---|
| Thioglycolic acid | 9.1 | 9.1 | 9.1 | 9.1 |  | 9.1 |
| Thiolactic acid |  |  |  |  | 10.6 |  |
| Oleocetyldimethyl-hydroxyethylammonium chloride in aqueous solution containing | 0.39 | 0.39 | 0.39 | 0.39 | 0.39 | 0.39 |

TABLE I-continued

| Example No. | 1 | 2 | 3 | 4 | 5 | 6 |
|---|---|---|---|---|---|---|
| 30% by weight of active matter |  |  |  |  |  |  |
| 1,3-Diaminopropane | 4.7 | 8.1 |  |  | 4.7 |  |
| N,N-Dimethyl-1,3-diaminopropane |  |  | 7.9 |  |  |  |
| N,N-Diethyl-1,3-diaminopropane |  |  |  | 8.6 |  |  |
| 2-Hydroxy-1,3-diaminopropane |  |  |  |  |  | 7.6 |
| Perfume, Peptizer | q.s. | q.s. | q.s. | q.s. | q.s. | q.s. |
| pH | 8.5 | 9.5 | 8.5 | 8.5 | 8.5 | 8.5 |
| Water q.s. | 100 | 100 | 100 | 100 | 100 | 100 |

It is found first of all that, in the case of each of the compositions defined above, the odor in use is considerably improved.

The use of these compositions is performed as follows: each composition is applied to hair wound onto curlers beforehand. The composition is allowed to act for 15 minutes and is then rinsed with water. An oxidizing solution of 8-volume aqueous hydrogen peroxide is then applied and allowed to act for 10 minutes. The hair is then rinsed with water and then unwound. It is found that the curling obtained is excellent and that the hair is in a good state. No inconvenience has been caused during the treatment by the odors originating from the alkalifying agent.

EXAMPLE 7

A comparative study of the effectiveness of the compositions of Examples 1 to 6 for curling hair was carried out in comparison with corresponding compositions in which the alkalifying agent employed was aqueous ammonia. In each case the quantity of aqueous ammonia employed in the comparative composition was that needed to obtain the pH shown for each of the formulations of Examples 1 to 6.

The study was carried out on wigs of human hair; the tresses were 15 cm in length. The standardized hair tresses were wound onto curlers 9 mm in diameter. The application of the compositions of Examples 1 to 6 and of the corresponding compositions produced with aqueous ammonia was carried out by following the procedure described for Examples 1 to 6.

At the end of the treatment the hair was unwound and the mean radius of curvature of the waving obtained was measured at mid-length of the wet tresses. The effectiveness of the test composition is proportionally greater the smaller the radius of curvature. The results are listed in Table II below:

TABLE II

| Example No. Nature of the alkalifier | 1 | 2 | 3 | 4 | 5 | 6 |
|---|---|---|---|---|---|---|
| Formula (I) | 0.66 | 0.50 | 0.68 | 0.88 | 3.50 | 0.66 |
| Aqueous ammonia | 1.16 | 0.57 | 1.16 | 1.16 | 6.00 | 1.16 |

It was found, furthermore, that by employing the alkalifying agents of formula (I) an improvement was obtained in the mechanical properties of the hair after treatment, when compared with the use of aqueous ammonia.

EXAMPLES 8 TO 11

4 compositions for bleaching or lightening hair were formulated by employing a compound of formula (I) as alkalifying agent in the case of each one. The formulations thus produced are given in grams in Table III below:

TABLE III

| EXAMPLE No. | 8 | 9 | 10 | 11 |
|---|---|---|---|---|
| 1,3-Diaminopropane | 4.0 | — | — | — |
| 2-Hydroxy-1,3-diaminopropane | — | 6.0 | — | — |
| N,N-Dimethyl-1,3-diaminopropane | — | — | 4.0 | — |
| N,N-Diethyl-1,3-diaminopropane | — | — | — | 4.0 |
| Oleyl alcohol polyglycerolated with 2 moles of glycerol | 4.0 | 4.0 | 4.0 | 4.0 |
| Oleyl alcohol polyglycerolated with 4 moles of glycerol | 4.4 | 4.4 | 4.4 | 4.4 |
| Oleic acid | 3.0 | 3.0 | 3.0 | 3.0 |
| Oleylamine oxyethyleneated with 2 moles of ethylene oxide, sold by Akzo under the name Ethomeen O12 | 7.0 | 7.0 | 7.0 | 7.0 |
| Oleyl alcohol | 5.0 | 5.0 | 5.0 | 5.0 |
| Oleyldiethanolamide | 12.0 | 12.0 | 12.0 | 12.0 |
| Ethyl alcohol | 10.0 | 10.0 | 10.0 | 10.0 |
| Propylene glycol monomethyl ether | 20.0 | 20.0 | 20.0 | 20.0 |
| Sodium metabisulphite as 35% aqueous solution | 0.46 | 0.46 | 0.46 | 0.46 |
| Sequestering agent q.s | | | | |
| Water q.s. | 100 | 100 | 100 | 100 |
| pH | 11.2 | 10.6 | 10.7 | 10.4 |

At the time of use the compositions of Examples 8 to 11 are mixed with an equal weight of 20-volume aqueous hydrogen peroxide. These compositions are applied to tresses of brown hair. After 30 minutes' interval the hair is rinsed, shampooed and dried.

The hair treated with the composition of Example 8 changes from brown to dark blond; that treated with the composition of Examples 9, 10 and 11 changes from brown to light brown.

It is found that the odor in use is considerably improved in the case of each of the compositions defined above.

EXAMPLE 12

Example of Hair Dyeing

Grey hair containing 90% of white is dyed by applying the following oxidation dye composition, containing 1,3-diaminopropane as alkalifying agent:

Dye formulation (A)

| | |
|---|---|
| Oleic acid (19 g) neutralized with monoethanolamine (7.2 g) to form a soap | |
| Oleyl alcohol | 9 g |
| Ethyl alcohol | 12.5 g |
| Triethanolamine lauryl sulphate containing 28% of active substance (AS) | 0.84 g AS |
| Oleyldiethanolamide | 8 g |
| Propylene glycol | 10 g |
| Oleocetyl alcohol oxyethyleneated with 30 moles of ethylene oxide | 2 g |
| Cationic polymer described and prepared according to French Patent 2,270,846, consisting of repeat units of formula:<br>$$\left[ -N^+(CH_3)_2-((CH_2)_3-N^+(CH_3)_2-(CH_2)_6- \right]\;\; Cl^-\;\;Cl^-$$<br>in solution containing 60% of AS | 2.2 g AS |
| Hydroquinone | 0.15 g |

| -continued | |
|---|---|
| 1-Phenyl-3-methyl-5-pyrazolone | 0.2 g |
| Sodium metabisulphite in aqueous solution containing 35% of AS | 0.46 g AS |
| 1,3-Diaminopropane | 8 g |
| Sequestering agent, perfume q.s. | |
| para-Phenylenediamine | 0.216 g |
| 6-(β-Hydroxyethyloxy)-1,3-diaminobenzene, 2HCl | 0.482 g |
| Water | q.s. 100 g |
| pH | 11 |

Oxidizing Formulation (B)

20-volume aqueous hydrogen peroxide at pH=3

28 g of the mixture of equal weights of formulations (A) and (B) are applied to 3 g of hair. The composition is allowed to act for 30 minutes. The hair is rinsed with water, a shampoo is applied and it is dried.

The hair is colored a bluish ashen blond or ashen blue dark blond, depending on whether natural or permanent-waved hair is involved.

It is found that the odor of the above coloring composition is considerably improved in use.

EXAMPLE 13

A hair-removing composition containing 1,3-diaminopropane as alkalifying agent was prepared, with the following composition:

Part a

| | |
|---|---|
| Calcium gluconate | 2.5 g |
| Urea | 10 g |
| Water | 40 g |

Part b

| | |
|---|---|
| Polyoxyethyleneated cetylstearyl alcohol | 11 g |

Part c

| | |
|---|---|
| Calcium carbonate | 6.15 g |

Part d

| | |
|---|---|
| Calcium oxide | 3.42 g |

Part e

| | |
|---|---|
| Thioglycolic acid | 4.23 g |
| Water | 10 g |

1,3-Diaminopropane q.s. pH=8.25

Part b is introduced at 75° C. into part a and stirring is applied. Part c is introduced into the mixture (a+b), stirring of the mixture thus formed being continued for 20 minutes at 70° C. Part d is introduced into the mixture (a+b+c); after dissolving the temperature is returned to 20° C. Part e is then added. Water is added to make up 100 g.

It is found that the odor is considerably improved in the case of the above composition.

EXAMPLE 14

Permanent waving is carried out using cysteamine as reducing agent with a pretreatment with the aid of a diaminopropane. The following compositions are applied successively to the hair:

Composition A

| | |
|---|---|
| Acetic acid | 6.1 g |
| 1,3-Diaminopropane q.s. pH | 8.5 |
| Demineralized water q.s. | 100 g |

This composition is applied to natural hair for 10 minutes. After rinsing, the composition B is applied.

Composition B

| | |
|---|---|
| Cysteamine hydrochloride | 11.3 g |
| Aqueous ammonia q.s. pH | 8.5 |
| Demineralized water q.s. | 100 g |

The hair is wound onto rollers. After 15 minutes' exposure it is rinsed and the fixing composition C is applied.

Composition C

| | |
|---|---|
| 8-volume aqueous hydrogen peroxide | 100 g |
| Citric acid q.s. pH | 3.0 |

After 5 minutes' exposure the hair is rinsed and unwound.

The tresses thus treated are left in the open air for 3 weeks at a temperature of 37° C. The odor released from the tresses is assessed by a panel of testers 1 minute after spraying with a water mist, in comparison with tresses which have undergone treatment only with compositions B and C. In the unanimous view of the testers the tresses treated with compositions B and C have a much more unpleasant odor than those treated with compositions A, B and C.

We claim:

1. A cosmetic composition for treatment of human keratinous organs comprising, in an aqueous medium having a pH ranging from 5 to 12.5 and being suitable for application to said human keratinous organs, (a) an active agent selected from the group consisting of a reducing agent, a dyeing agent and an oxidizing agent, and (b) at least one diaminoalkane having the formula $$\begin{matrix} R_1 & & R_3 \\ & \diagdown & \diagup \\ & N-R-N & \\ & \diagup & \diagdown \\ R_2 & & R_4 \end{matrix} \quad (I)$$

wherein

R represents propylene optionally substituted by hydroxyl or $C_1$–$C_4$ alkyl, $R_1$, $R_2$, $R_3$ and $R_4$, each independently, represent hydrogen, $C_1$–$C_4$ alkyl or $C_1$–$C_4$ hydroxyalkyl, said diaminoalkane being present in an amount ranging from 3.7 to 12%, based on the weight of the total composition.

2. The cosmetic composition of claim 1 wherein said diaminoalkane is selected from the group consisting of 1,3-diaminopropane, N,N'-diethyl-1,3-diaminopropane, N,N-diethyl-1,3-diaminopropane, N,N-dimethyl-1,3-diaminopropane, 2-hydroxy-1-(N,N-diethyl)amino-3-aminopropane, 2-hydroxy-N,N'-di-tert-butyl-1,3-diaminopropane, 2-hydroxy-N,N'-tetramethyl-1,3-diaminopropane and 2-hydroxy-1,3-diaminopropane.

3. The cosmetic composition of claim 1 for the permanent deformation or removal of human keratinous organs wherein said active agent is a reducing agent selected from the group consisting of thioglycolic acid, thiolactic acid, cysteamine, cysteine, 4-hydroxy-N-(2-mercaptoethyl) butyramide, N-mono substituted 4-mercaptobutyramide and N,N-disubstituted 4-mercaptobutyramide.

4. The composition of claim 3 for the permanent deformation of human keratinous organs, said composition having a pH ranging from 5 to 10 and said diaminoalkane being present in an amount ranging from 3.7 to 12 percent by weight based on the total weight of said composition.

5. The composition of claim 3 for removal of human keratinous organs, said composition having a pH ranging from 9 to 12.5.

6. The cosmetic composition of claim 1 for dyeing human keratinous organs wherein said active agent is a dying agent selected from the group consisting of an orthophenylenediamine, a para-phenylenediamine, an orthoaminophenol, a paraaminophenol, an aromatic meta-diamine, a meta-aminophenol, a meta-diphenol, and a 5,6-dihydroxyindole, said composition having a pH ranging from 5 to 11 and said diaminoalkane being present in an amount ranging from 4 to 10 percent by weight based on the total weight of said composition.

7. The cosmetic composition of claim 1 for bleaching or lightening human keratinous organs wherein said active agent is an oxidizing agent, said composition having a pH ranging from 7 to 11.

* * * * *